United States Patent [19]

Clark et al.

[11] Patent Number: 5,837,452

[45] Date of Patent: Nov. 17, 1998

[54] METHODS FOR EXTRACTING NUCLEIC ACIDS FROM A WIDE RANGE OF ORGANISMS BY NONLYTIC PERMEABILIZATION

[75] Inventors: Kathleen A. Clark, Cardiff by the Sea; Daniel L. Kacian, San Diego, both of Calif.

[73] Assignee: Gen-Probe Incorporated, San Diego, Calif.

[21] Appl. No.: 778,582

[22] Filed: Jan. 3, 1997

Related U.S. Application Data

[60] Continuation of Ser. No. 433,149, May 3, 1995, abandoned, which is a division of Ser. No. 390,826, Feb. 17, 1995, abandoned, which is a continuation of Ser. No. 158,940, Nov. 29, 1993, abandoned.

[51] Int. Cl.$^6$ .............................. C12Q 1/68; C12N 1/00; C12N 1/06; B01F 17/00
[52] U.S. Cl. .............................. 435/6; 435/243; 435/259; 424/9.1; 252/351
[58] Field of Search ............................... 435/6, 243, 259; 424/9.1; 935/19, 20, 21; 252/351

[56] References Cited

U.S. PATENT DOCUMENTS

| | | | |
|---|---|---|---|
| 4,486,539 | 12/1984 | Ranki et al. ............................... | 436/504 |
| 4,830,969 | 5/1989 | Holmes ..................................... | 435/259 |
| 5,212,059 | 5/1993 | Schwartz et al. ............................ | 435/6 |
| 5,231,015 | 7/1993 | Cummins et al. ...................... | 435/91.2 |

FOREIGN PATENT DOCUMENTS

| | | |
|---|---|---|
| 0149514 | 1/1985 | European Pat. Off. . |
| 0428197 | 5/1991 | European Pat. Off. . |
| 0547789 | 11/1992 | European Pat. Off. . |
| 4-349892 | 5/1991 | Japan . |
| 9207096 | 10/1993 | WIPO . |

OTHER PUBLICATIONS

Derwent Publication Ltd London GB, Data Base WPI, Abstract. Week DW9303, JP4349892 (1992).

H. Meijer, et al., "*Recovery and Identification of DNA Sequences Harboured In Preserved Ancient Human Bones*", Biochem. Biophys. Res. Commun., 183 : (2) :367–374, (Mar. 16, 1992).

Mifflin et al, "Use and application of nucleic acid probes in the clinical laboratory", Clin. Chem. 35(9):1819–1825, 1989.

Doi et al., "Isolation of nuclei from a tetraploid strain of *saccharomyces cerevisiae*", J. Biochem. 75:1017–1026, 1974.

Ulenhopp, et al., Viscoelastic Charactization of Single–Stranded DNA. Biophys. J. 15:223–232 (1975).

Godson, et al., Lysis of *E. Coli* with a neutral detergent. Biochem. Biophys. Acta 149:476–088 (1967).

Lindblom et al, (1988), "Rapid DNA purification for restriction fragment length polymurphism analysis", Gene Anal. Techn. 5:97–101.

Ortlepp et al, (1989), "An Improved boiling method for the preparation of bacterial plasmid and phage DNA", Gene Anal. Techn. 6:96–96.

Arnold et al, (1989), "*Assay formats involving acridinium ester labeled probes*", Clin. Chem. 35(8):1588–1594.

Stratigene Catalog, (1988), "Gene characterization kits", p. 39.

Darnell et al. (1986), "RNA synthesis and processing in eukaryotes", in Molecular Cell Biology, Scientific American Books, New York, pp. 322–323.

New England Biolabs catalog, (1992), p. 73.

Sritharan et al, (1991) "A simple method for diagnosising *M. tuberculosis* infection in clinical samples using PCR", Mol. Cell. Probes 5:385–395.

*Primary Examiner*—W. Gary Jones
*Assistant Examiner*—Jeffrey Fredman
*Attorney, Agent, or Firm*—Carlos A. Fisher; Charles B. Cappellari

[57] ABSTRACT

Methods for extracting nucleic acids by heating sample cells at about 80–95 degrees C. in a permeabilization reagent containing a non-ionic detergent and a metal chelating agent. The methods of the invention release large fragments of undegraded nucleic acids without physically disrupting the entire cell wall. The nucleic acids are released into solution without bursting the cells and are suitable for research and testing without further purification. The extraction method described herein is rapid, easy to perform, and applicable to a wide variety of cells, including microorganisms. Clinical samples may be screened for the presence or absence of a microorganism by heating the sample at 80–95 degrees Celsius in the presence of a non-ionic detergent and a metal chelating agent, adding to the sample a nucleic acid probe specific to the selected microorganism, incubating the sample under conditions which allow the probe to hybridize to released nucleic acid and detecting whether any hybridized probe is present. A kit for performing the nucleic acid extraction methods disclosed herein is also described.

20 Claims, 6 Drawing Sheets

|   | B | C | E | F |
|---|---|---|---|---|
| 1 | ATCC# | NAME | GAS Results | ALL BAC/FUNG |
| 2 | 33604 | Acinetobacter calcoaceticus | NEG | POS |
| 3 | 153309 | Acinetobacter lwoffii | NEG | POS |
| 4 | 10049 | Actinomyces israleii | NEG | POS |
| 5 | 19411 | Actinomyces pyogenes | NEG | POS |
| 6 | 11563 | Aerococcus viridans | NEG | POS |
| 7 | 7966 | Aeromonas hydrophila | NEG | POS |
| 8 | 27061 | Alcaligenes denitrificans | NEG | POS |
| 9 | 8750 | Alcaligenes faecalis | NEG | POS |
| 10 | 6051 | Bacillus subtilis | NEG | POS |
| 11 | 23745 | Bacteroides fragilis | NEG | POS |
| 12 | 10580 | Bordetella bronchiseptica | NEG | POS |
| 13 | 25238 | Branhamella catarrhalis | NEG | POS |
| 14 | 9172 | Brevibacterium linens | NEG | POS |
| 15 | 33560 | Campylobacter jejuni | NEG | POS |
| 16 | 18804 | Candida albicans | NEG | POS |
| 17 | 1147 | Capnocytophaga ochracea | NEG | POS |
| 18 | 29094 | Chromobacterium violaceum | NEG | POS |
| 19 | 14501 | Clostridium innocuum | NEG | POS |
| 20 | 13124 | Clostridium perfringens | NEG | POS |
| 21 | 25582 | Clostridium ramosum | NEG | POS |
| 22 | 11913 | Corynebacterium diphtheriae | NEG | POS |
| 23 | 9345 | Corynebacterium haemolyticum | NEG | POS |

FIG. 4A

|  | B | C | E | F |
|---|---|---|---|---|
| 24 | 10700 | Corynebacterium pseudodiphtheriticum | NEG | POS |
| 25 | 19410 | Corynebacterium pseudotuberculosis | NEG | POS |
| 26 | 373 | Corynebacterium xerosis | NEG | POS |
| 27 | 32045 | Cryptococcus neoformans | NEG | POS |
| 28 | 35073 | Deinococcus radiodurans | NEG | POS |
| 29 | 19433 | Enterococcus faecalis | NEG | POS |
| 30 | 19414 | Erysipelothrix rhusiopathiae | NEG | POS |
| 31 | 10798 | Escherichia coli | NEG | POS |
| 32 | 13253 | Flavobacterium meningosepticum | NEG | POS |
| 33 | 10379 | Gemella haemolysans | NEG | POS |
| 34 | 19418 | Haemophilus influenzae | NEG | POS |
| 35 | 23357 | Klebsiella pneumoniae | NEG | POS |
| 36 | 4356 | Lactobacillus acidophilus | NEG | POS |
| 37 | 19257 | Lactococcus lactis cremoris | NEG | POS |
| 38 | 33152 | Legionella pneumophila | NEG | POS |
| 39 | 33313 | Leuconostoc paramesenteroides | NEG | POS |
| 40 | 35152 | Listeria monocytogenes | NEG | POS |
| 41 | 27570 | Micrococcus kristinae | NEG | POS |
| 42 | 4698 | Micrococcus luteus | NEG | POS |
| 43 | 14470 | Mycobacterium gordonae | NEG | POS |
| 44 | 25177 | Mycobacterium tuberculosis | NEG | POS |
| 45 | 13077 | Neisseria meningitidis | NEG | POS |
| 46 | 19247 | Nocardia asteroides | NEG | POS |
| 47 | 33225 | Oerskovia turbata | NEG | POS |

FIG. 4B

|    | B     | C                          | E   | F   |
|----|-------|----------------------------|-----|-----|
| 48 | 27402 | Oerskovia xanthineolytica  | Neg | Pos |
| 49 | 17741 | Paracoccus denitrificans   | Neg | Pos |
| 50 | 33314 | Pediococcus acidilactici   | Neg | Pos |
| 51 | 27337 | Peptostreptococcus anaerobius | Neg | Pos |
| 52 | 14955 | Peptostreptococcus magnus  | Neg | Pos |
| 53 | 6919  | Propionibacterium acnes    | Neg | Pos |
| 54 | 25933 | Proteus mirabilis          | Neg | Pos |
| 55 | 25330 | Pseudomonas aeruginosa     | Neg | Pos |
| 56 | 33071 | Rahnella aquatilis         | Neg | Pos |
| 57 | 25592 | Rhodococcus bronchialis    | Neg | Pos |
| 58 | 11170 | Rhodospirillum rubrum      | Neg | Pos |
| 59 | 12598 | Staphylococcus aureus      | Neg | Pos |
| 60 | 33591 | Staphylococcus aureus      | Neg | Pos |
| 61 | 25923 | Staphylococcus aureus      | Neg | Pos |
| 62 | 12228 | Staphylococcus epidermidis | Neg | Pos |
| 63 | 13813 | Streptococcus agalactiae   | Neg | Pos |
| 64 | 9811  | Streptococcus mitis        | Neg | Pos |
| 65 | 6303  | Streptococcus pneumoniae   | Neg | Pos |
| 66 | 19615 | Streptococcus pyogenes     | Neg | Pos |
| 67 | 10556 | Streptococcus sanguis      | Neg | Pos |
| 68 | 23345 | Streptomyces griseus       | Neg | Pos |
| 69 | 17802 | Vibrio parahaemolyticus    | Neg | Pos |
| 70 | 9610  | Yersinia enterocolitica    | Neg | Pos |

FIG. 4C

METHODS FOR EXTRACTING NUCLEIC ACIDS FROM A WIDE RANGE OF ORGANISMS BY NONLYTIC PERMEABILIZATION

This application is a file-wrapper continuation application of application Ser. No. 08/433,149, filed May 3, 1995, entitled "Methods for Extracting Nucleic Acids From A Wide Range of Organisms", now abandoned, which is a divisional of application Ser. No. 08/390,826, filed Feb. 17,1995, entitled "Methods for Extracting Nucleic Acids From A Wide Range of Organisms", now abandoned which is a continuation of application Ser. No. 08/158,940, filed on Nov. 29, 1993, entitled "Methods For Extracting Nucleic Acids From A Wide Range of Organisms", now abandoned.

BACKGROUND OF THE INVENTION

Technical Field of the Invention

The present invention relates to methods for extracting nucleic acids of a wide range of organisms from cultures, clinical specimens, and other samples, suitable for use in nucleic acid hybridization procedures and other diagnostic techniques for specifically identifying tested organisms. The present invention further relates to diagnostic kits employing permeablization reagents suitable for extracting nucleic acids from a wide range of organisms, such nucleic acids being suitable for subsequent hybridization, detection, and quantitative identification of the assayed organisms.

Background Art

The advent of modern techniques of molecular biology and genetic engineering has caused a revolution in the diagnosis of disease. In recent years the identification of pathogenic organisms, especially microorganisms such as bacteria and yeast, has become much faster and more accurate as increasingly advanced methods for detecting, quantifying, and distinguishing between species and subspecies of microorganisms have been developed. Many, if not most, of these diagnostic techniques exploit inherent differences between the nucleic acid sequences of different species of pathogenic agents, and between pathogenic and non-pathogenic microorganisms. The speed, selectivity and sensitivity of these nucleic acid-based diagnostic methods has resulted in faster and more accurate patient treatment, and hence a more healthy public.

Diagnostic kits relying primarily on nucleic acid hybridization have been developed for the diagnosis of a number of diseases in which microscopic organisms are implicated, either as a causative agent or as an indicator of the disease. While not intended to be an exhaustive listing, kits are thus available or contemplated for the detection and/or the identification of the microorganisms responsible for tuberculosis (*Mycobacterium tuberculosis*), common sexually transmitted diseases (*Chlamydia trachomatis, Neisseria gonorrhoeae*), respiratory illnesses (*Mycoplasma pneumoniae*), pharyngitis and rheumatic fever (Group A Streptococcus(*S. pyogenes*)), epiglottitis (*Haemophilus influenzae*) as well as viruses such as the causative agent of ARC and AIDS (HIV). All such methods require the target nucleic acids to be readily available for hybridization.

Most methods for extracting microbial nucleic acids involve bursting the microorganism's cell wall (lysis) and extracting the contents of the cell into a buffered solution. Lipids, carbohydrates, and proteins can then be removed from solution by performing a phenol extraction, and the nucleic acids further purified by precipitation with cold ethanol. The precise methods for bursting, or lysing, the microorganism commonly depend on the nature of the organism itself; until recently, however, studies were largely limited to a single Gram-negative bacterial species: *Escherichia coli*. (See Stent, Gunther S. & Calendar, Richard, *Molecular Genetics* 51 (2d ed. 1978)).

Extraction of nucleic acids from Gram-negative bacteria such as *E. coli* has traditionally involved: (a) the use of shear or mechanical forces as in ultrasonication, grinding with abrasives, shaking with glass beads, and the French pressure cell; (b) weakening the cell wall, either by one or more rounds of freezing and thawing or by treatment with a lysing enzyme such as lysozyme, followed by dissolution of the cell membrane by treatment with a strong detergent or a chaotropic reagent (i.e. a reagent that disrupts hydrophobic interactions). In both such methods, the contents of the lysate include organelles, proteins (including enzymes such as proteases and nucleases), carbohydrates, and lipids as well as nucleic acids, which may necessitate further purification of the nucleic acids.

A method involving detergent-aided enzymatic lysis of *E. coli* cells, (*Lysis of Escherichia coli with a Neutral Detergent*, Godson, G. N. & Sinsheimer, R. I., 149 Biochem. Biophys. Acta 476 (1967)) has been described. Schein, (EPO publication No. 0061250), describes a method for recovering recombinant proteins from host organisms using lysozyme, chaotropic agents, and/or detergents; the host bacteria were *E. coli* strains.

Lysis of Gram-positive microorganisms is considerably more difficult than for Gram-negative bacteria, due to a thicker and denser layer of peptidoglycan, a major bacterial cell wall component. Lysis of some Gram-positive microorganisms using lytic enzymes has been reported. (See e.g., *Lysis of Grouped and Ungrouped Streptococci by Lysozyme,* Coleman, S. E. et al., 2 Infect. and Immun. 563–569 (1970); *Method for the Lysis of Gram-Positive, Asporogenous Bacteria with Lysozyme,* Chassy, Bruce M. and Giuffrida, Alfred, 39 Applied and Env. Micro. 153–158 (1980); *Lysis of Streptococcus mutans cells with Mutanolysin, a Lytic Enzyme prepared from a Culture Liquor of Streptomyces gloisporus* 1829, Hamada, S. et al., 23 Archs. Oral Biol. 543–549 (1978); *Lysis and Protoplast Formation of Group B Streptococci by Mutanolysin,* Calandra, G. B. and Cole, R. M., 28 Infect. and Immun. 1033–1037 (1980)).

Non-enzymatic compositions have been described where clinical samples containing Gram-negative pathogenic bacteria were treated with a solution containing a chaotrope, (guanidium thiocyanate (GuSCN)); an anionic detergent, (sodium dodecyl sulphate (SDS) or N-lauorylsarcosine (sarcosyl)); a divalent metal chelating agent, (ethylenediaminetetracetic acid (EDTA)); and a reducing agent, (β-mercaptoethanol). (Schwartz et al., U.S. Pat. No. 5,212,059). Such compositions are described as lysis/hybridization solutions wherein the entire sample is used in a single assay.

The cell wall of yeast species, which can contain β-glucans and chitin as major components, differs in composition from that of bacteria; thus, enzymatic methods for the extraction of nucleic acids from yeast often involve a set of entirely different enzymes, such as zymolyase, with different specificities than those used to lyse bacteria.

Sheiness and Levine, (PCT application Wo 92/07096) describe a diagnostic kit for the detection of vaginal pathogens. The tested organisms were species of Candida, a yeast; *Gardnerella vaginalis,* a Gram-negative bacterium and *Trichomonas vaginalis,* a eukaryotic protozoan without a cell wall. The solution they used was reportedly capable of liberating nucleic acids from each of these organisms as detected by nucleic acid hybridization.

Holmes, U.S. Pat. No. 4,830,969, describes a process for the isolation of nucleic acids by boiling cultured cells in a "lysing agent".

Wase, (EPO Publication No. 0149514), discloses a method of manufacturing a flocculating agent from a lysed bacterial cell culture. One of the various described methods of initiating cell lysis is by the use of heat.

The use of heat alone has been shown to be effective to produce intact DNA suitable for further biochemical manipulation from certain bacteria, the genus Mycobacteria, considered by many workers to be difficult to lyse. (Robson, EPO Publication No. 0547789A1).

All of the aforementioned methods lack the benefit of a single reagent capable of causing the release of nucleic acids, (e.g. ribosomal RNA and/or DNA encoding ribosomal RNA sequences), from a wide range of microorganisms in biological samples in a form suitable for nucleic acid hybridization without the need for subsequent phenol extraction and ethanol precipitation procedures.

SUMMARY OF THE INVENTION

The present invention concerns the use of a permeabilization reagent capable of liberating nucleic acids, (e.g., RNA and DNA, preferably ribosomal RNA and/or DNA encoding ribosomal RNA sequences) from a wide variety of organisms including Gram-positive and Gram-negative bacteria and yeast. The reagent need not contain lytic enzymes, and can be used at high temperatures; preferably between about 80° and 100° C., more preferably between about 80° and 95° C.; most preferably about 95° C. The present invention is also directed to methods and kits involving the permeabilization reagent for the extraction of nucleic acids, preferably ribosomal RNA and/or DNA encoding ribosomal RNA sequences, from a wide range of organisms including Gram-positive and Gram-negative bacteria and yeast. The liberated nucleic acids may then be used for various purposes, including but not limited to nucleic acid amplification methods such as the polymerase chain reaction (PCR), or hybridization with a probe oligonucleotide having a nucleotide sequence complementary to a specific nucleotide sequence of the liberated nucleic acids. Hence, the compositions, methods, and kits herein described are designed to allow rapid, simple preparation of nucleic acids from the organisms contained in the sample.

The advantages of a single nucleic acid extraction method for use with a wide range of microorganisms include a) reducing the time and expense involved in training laboratory technicians to perform diagnostic tests; b) lowering the costs of manufacturing, since a single permeabilization reagent can now be used in multiple products, and c) reducing the cost and time associated with the quality control of enzyme-based extraction reagents. Thus a first object of the present invention is to provide a single reagent able to induce the release of detectable amounts of nucleic acids from a wide variety of microorganisms.

Many diagnostic kits still depend on the use of enzymes to liberate nucleic acids from cells. If the yield of the target nucleic acids available for hybridization is not good, whether through inefficient enzymatic lysis, because a particular sample does not contain many assayable cells, because the target microorganism or nucleic acid is present in only a subpopulation of the cells, or otherwise, the sensitivity of the diagnostic system can decrease. Thus, a second object of the present invention is to provide a nucleic acid extraction method that gives a yield of the target nucleic acid which is as good or better than other comparable methods.

A third object of the present invention is a nucleic acid extraction method that can be inexpensively produced for inclusion in a commercial diagnostic assay kit. The permeabilization reagent used in conjunction with the method of the present invention makes use of relatively inexpensive laboratory chemicals and need not include expensive lytic enzymes.

It is a fourth object of the present invention to provide a gentle, simple method for causing cells to liberate nucleic acids into solution. Because the method of the present invention leaves the cell wall of many target microorganisms substantially intact following the extraction step, the liberated nucleic acids are not commingled with other unwanted cellular components. Most unwanted cellular matter remains within the cell; the nucleic acids in the supernatant may be separated from the cells by centrifugation and separately assayed, although this is not essential to the practice of the present method. The present invention is also quick and simple, enabling both skilled and unskilled laboratory workers to extract nucleic acids, particularly ribosomal RNA and/or DNA encoding ribosomal RNA sequences, in a single step. Moreover, the present extraction method is mild to the nucleic acids, producing nucleic acids which are suitable for subsequent use, as in hybridization assays, without the need for additional purification.

Because it is preferable to minimize the exposure of the laboratory technician to potentially harmful microorganisms in the first step of the diagnostic assay, it is a fifth object of the present invention to provide a relatively safe method of extracting nucleic acids from clinical samples. This is done in two ways: by minimizing the time necessary to liberate the majority of the target nucleic acid from the target cells, and by conducting the permeabilization step at temperatures high enough to quickly kill the majority of the pathogens (i.e. temperatures between about 80° and 100° C.).

The present invention is applicable to organisms other than Gram-positive and Gram-negative bacteria and yeast; for example mycoplasma, protozoa, and enveloped viruses as well as other cells, such as cultured eukaryotic cells, having a less substantial cell wall than bacteria or yeasts, or no cell wall at all may be permeabilized by the method of the present invention. While still gentle, in such cases the present method may cause more damage to the cell wall or membrane than occurs with bacteria or yeasts.

Definitions

The following terms have the following meanings for the purposes of this application, unless expressly stated to the contrary herein.

By "enzymatic lysis" is meant the breaking open of a cell or a group of cells, or the liberation of some or all of the intracellular components following treatment of the cell or cells with an enzyme which completely or partially digests the organism's cell wall.

By "detergent" is meant a molecule or class of molecules which have a hydrophobic region or moiety capable of interacting with hydrophobic solvents and the hydrophobic portions of cellular membranes, and a hydrophilic region or moiety which may have a positive or a negative charge in solution, or alternately may have a polar region with no charge at all.

By "non-ionic detergent" is meant a detergent containing at least one polar, uncharged group or ion in its hydrophilic region or moiety.

By "ionic detergent" is meant a detergent containing at least one positive or negatively charged group or ion in hydrophilic region or moiety.

By "metal chelating agent" or "chelating agent" is meant a molecule or class of molecules which are capable of binding, complexing, or coordinating with metal ions, thereby reducing the effective concentration of the metal ions in solution.

Reference to the "release of nucleic acids" is intended to mean the liberation of nucleic acids in sufficient quantities such that the method of release is useful for nucleic acid hybridization assays.

By "nucleic acid" or "nucleic acids" is meant polydeoxyribonucleotides or polyribonucleotides of at least two, and preferably 10 or more nucleotides in length. The term "nucleic acid" includes polynucleotides, oligonucleotides, and DNA or RNA molecules. The term "nucleic acid" can refer to either single-stranded or double-stranded polynucleotides, or both.

By "target nucleic acid" is meant a nucleic acid comprising a target nucleic acid sequence sought to be detected. Preferably such sequences are characteristic of a particular organism.

By "target nucleic acid sequence" or "target sequence" is meant a specific nucleic acid sequence, or the nucleic acid sequence complementary thereto.

By "target organism" is meant any species of prokaryotic or eukaryotic organism, or any virus, sought to be identified using the methods herein described. While not exclusively, generally such organisms will be contained in a biological sample, such as in scrapings, or swabs. Preferably the organism will be a pathogenic microorganism.

By "biological sample" is meant any specimen or sample containing substances of animal, vegetal, bacterial, viral, or protist origin. Such samples include, but are not limited to, food or agricultural samples; environmental samples; samples containing body fluids, secretions or excretions such as urine, blood, milk, cerebrospinal fluid, sputum, saliva, stool, lung aspirates, tears, lymphatic fluid, or semen; throat or genital swabs; and bacterial, viral, plant or animal cell cultures, suspensions or lysates. A biological sample may or may not contain ribonucleases.

By "clinical sample" is meant a biological sample obtained from a human or animal for testing or examination for the purposes of diagnosing or managing disease.

By "complementary" is meant having a nucleic acid sequence whereby stable hydrogen bonds are formed between the nucleotide bases of a region of one nucleic acid strand and those of a region of another nucleic acid strand under conditions suitable for nucleic acid hybridization. That is, hydrogen bonds are most commonly formed between an adenosine(A) residue on one strand and a thymine(T) or uracil(U) residue on another strand, and between a guanine(G) residue on one strand and a cytosine (C) residue on another strand. Such regions of complementarity generally involve between about 15 and 100 or more contiguous nucleotides of each nucleic acid strand.

By "sufficiently complementary" is meant capable of forming a double-stranded hydrogen-bonded region under conditions suitable for nucleic acid hybridization. While two nucleic acid strands are sufficiently complementary if they have 100% complementarity over specific contiguous and corresponding regions, two single stranded nucleic acids having regions of less than 100% complementarity can form a double-stranded region under hybridization conditions. Such regions, not 100% complementary but able to form stable double stranded regions under hybridization conditions, are hereby considered sufficiently complementary.

By "lysis" is meant cellular dissociation involving physical disruption and breakage of the cell wall and/or membrane, causing intracellular components including nucleic acids to be released into the surrounding medium.

By "permeabilization" or "permeabilize" is meant dissociation of the cell wall and/or membrane resulting in the release of detectable amounts of nucleic acids from the cell into the surrounding medium.

By "permeabilization reagent" is meant a chemical or physical agent, or both, which is capable of causing the permeabilization of a cell or group of cells.

By "selection reagent" is meant a reagent used in a procedure capable of chemically or physically differentiating between hybridized double-stranded nucleic acid regions comprising a nucleic acid probe and unhybridized, single-stranded nucleic acids and/or nucleic acid probes.

By "detection reagent" is meant a reagent used in a procedure capable of detecting nucleic acids having a double-stranded nucleic acid region in which one strand is a nucleic acid probe.

By "probe reagent" is meant a reagent containing a nucleic acid probe having a nucleotide sequence sufficiently complementary to the nucleotide sequence of a target nucleic acid, such probe usually having a reporter group or moiety capable of detection in a hybridization assay.

One aspect of the present invention relates to non-enzymatic methods for inducing a wide variety of microorganisms to release nucleic acids, preferably ribosomal RNA and/or DNA encoding ribosomal RNA sequences, into solution. In one example, a sample containing cells to be identified is mixed with an extraction solution containing a non-ionic detergent and a metal chelating agent. The suspension is heated to a temperature from about 85°–95° C. for about 5 to 15 minutes. Upon heating, the nucleic acids are released into solution without observable destruction to the cell wall of the sample cells when observed under the microscope. The nucleic acids so liberated are suitable for hybridization, amplification, or other genetic manipulations without further purification.

The present invention provides a rapid, inexpensive and mild method for extracting nucleic acids from microorganisms. By eliminating the use of enzymes to perform the extraction step, the cost, variability, and difficulty associated with enzyme-mediated extraction of nucleic acids is significantly reduced.

Furthermore, the present invention eliminates the necessity for chaotropic agents as part of a lysis or permeabilization reagent. Chaotropic agents are generally used at very high concentrations, and are expensive. Due to these high concentrations, chaotropes can precipitate from the extraction solution during shipment or storage of the diagnostic kit. Chaotropes used to extract nucleic acids can change the conditions necessary for subsequent hybridization of the probe and target nucleic acid, and may be completely incompatible with the use of the extracted nucleic acids in enzyme-mediated reactions such as PCR or other target amplification methods. In the latter case it may be necessary to separate the chaotrope from the extracted nucleic acid, which would add a removal step to the entire protocol and increase the chance for an erroneous result. Moreover, chaotropes such as GuSCN are difficult to pipette because of their high viscosity. Thus, the absence of chaotropes in a method for extracting nucleic acids in a clinical sample is economically and logistically useful.

In a second aspect, the microorganisms to be assayed may be obtained from a clinical sample or other biological material that may contain nucleases, for example ribonucleases. Preferably, the present invention relates to methods for preparing clinical throat and genital swab specimens for the identification of microorganisms by probe hybridization to nucleic acids released from the assayed microorganisms. In this case, the entire swab may be contacted with, or immersed in the permeabilization solution containing a non-ionic detergent and a metal chelating agent. If the desired target nucleic acid is RNA, the permeabilization reagent is accompanied by the further addition of an anionic detergent, such as lithium lauryl sulphate, or sodium dodecyl sulphate. The anionic detergent may inactivate nucleases present in the clinical specimen which degrade the target nucleic acid. The swab in the permeabilization solution may then be heated to about 80°–95° C. for about 5–30 minutes, resulting in the release of nucleic acids from the microorganism.

The speed and temperature of the nucleic acid extraction step serves to reduce the exposure of laboratory technicians to infectious organisms. At the described temperature of 80°–95° C., the majority of the organisms in the sample, potentially including such pathogenic organisms as HIV and the causative agents of hepatitis and tuberculosis, will be killed. Since the extraction method is rapid and can be carried out without repeated transfer of cell suspensions from tube to tube, potential exposure is additionally reduced.

Another aspect of the present invention is a kit including reagents for conducting the described extraction method, and for subsequently identifying whether particular microorganisms are present in a sample. The kit contains a permeabilization reagent, a probe reagent, a selection reagent, and a detection reagent. The kit may include a supply of a permeabilization solution containing an ionic detergent, a non-ionic detergent and a metal chelating agent, and a supply of reagents necessary to detect and identify the target nucleic acid. Preferably, the identification and detection reagents include a probe reagent containing at least one species of nucleic acid probe sufficiently complementary to one or more nucleic acid sequences specific to the ribosomal RNA of the target microorganism. (See e.g., Hogan et al., U.S. Pat. No. 5,216,143 and Milliman and Hammond, U.S. Pat. No. 5,232,831, each of which is incorporated by reference herein.) Probe reagents containing derivitized nucleic acid probes (such as those containing phosphorothioate and/or methylphosphonate linkages) capable of recognizing and binding to specific nucleic acid sequences are known to those skilled in the art, and are contemplated to be capable of use in kits with the present extraction method.

Other features, uses and advantages of the invention will be apparent to one skilled in the art from the following description of the preferred embodiments, the figures and the claims.

BRIEF DESCRIPTION OF THE FIGURES

FIGS. 4A, 4B and 4C comprise a single table listing a panel of microorganisms permeabilized in accordance with the methods described herein and showing the applicability of these permeabilization methods to a wide range of microorganisms.

DETAILED DESCRIPTION OF THE INVENTION

Figure 1:
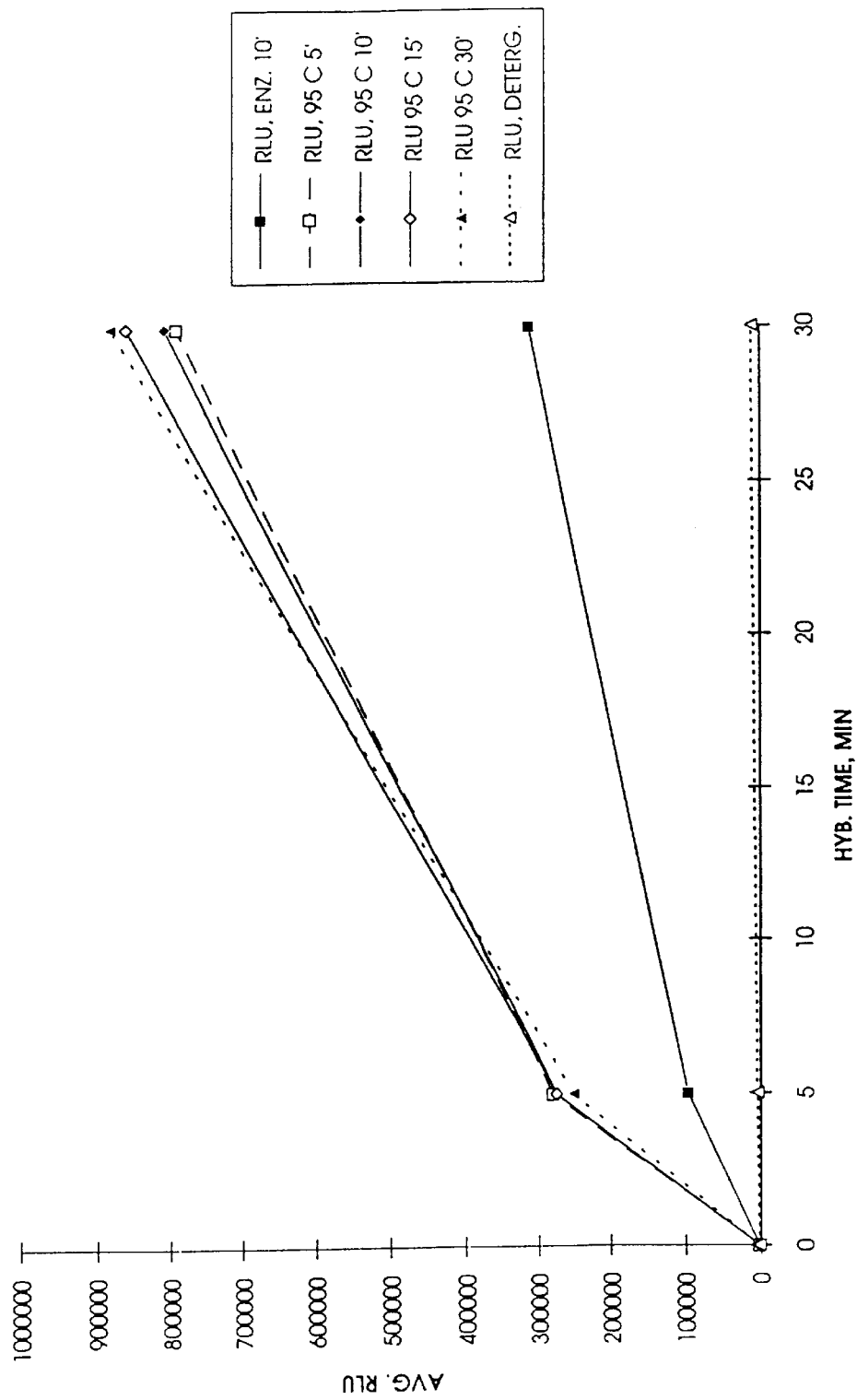
FIG. 1 is a graphical representation of an experiment quantifying the release of target nucleic acid (ribosomal RNA) from a Gram-positive microorganism, *Streptococcus pyogenes*, incubated for varying amounts of time at 95° C.

The claimed methods and kit feature the use of a permeabilization reagent for inducing the release of nucleic acids from a wide variety of microorganisms, and for the subsequent detection and identification of nucleic acid sequences specific to a target microorganism, class of target microorganisms, or to multiple different target microorganisms, as well as a combination of apparatus, media and agents for accomplishing such methods. The various steps, media and agents are discussed generally above; descriptions of the preferred embodiments are now provided. These descriptions are provided for the purpose of illustration only, and are not intended to limit the present invention in any way, the invention being defined solely by the claims which conclude this specification.

Extraction of Nucleic Acids from the Desired Cells The target microorganisms from which the nucleic acids are to be extracted may be obtained from a variety of sources. It is not essential that the cells to be assayed are contained in medical samples; those of ordinary skill in the art will recognize that a sample of any origin is applicable to the present invention provided it contains the target microorganism (and thus the target nucleic acid) in quantities sufficient to be detected by the particular means for detection used in a given system. If an amplification procedure such as the polymerase chain reaction (PCR), or a transcription-based method is to be used prior to the detection step, the original sample may correspondingly contain relatively few target microorganisms or target nucleic acids. See e.g., American Society for Microbiology, *Diagnostic Molecular Microbiology: Principles and Applications* 56–70(1993), which is hereby incorporated by reference.

For biological or physiological samples, the methods of the present invention may be employed using all types of physiological specimens including but not limited to cells or microorganisms grown in culture, blood, tissue, saliva, sputum, feces, spinal or synovial fluids, serum, urine, or other fluids. Such physiological specimens may be obtained from human, animal, or plant sources. Environmental or food samples may also be used according to the present methods to release nucleic acids from microorganisms present in these samples. Preferably, the present invention is used to release nucleic acids from microorganisms contained in a clinical oral or genital swab.

After obtaining a cell sample, the cell sample is contacted with or placed into a permeabilization reagent and heated to about 80°–95° C. until nucleic acids are released from the cells. The permeabilization reagent as used herein can consist, for example, of a saline solution, an EDTA solution or a non-ionic detergent solution. Nucleic acids ( e.g. RNA and DNA, preferably ribosomal RNA and DNA encoding ribosomal RNA sequences) can be extracted from samples containing target microorganisms using the present method with any of these permeabilization reagents. Thus, a variety of permeabilization reagents can be employed to extract nucleic acids from cells using the methods described herein.

Preferably, the permeabilization reagent comprises the combination of a non-ionic detergent and a metal chelating agent. Applicants have found that the combination of these two reagents optimize the amount of undegraded nucleic acid that is extracted from the cell sample. A non-ionic detergent is a detergent that is uncharged when dissolved in solution. Applicants have successfully practiced the present nucleic acid extraction methods using non-ionic detergents such as polyoxyethylene ethers (sold under the trade names Triton X-100 and Triton X-102 by Sigma Co., St. Louis, Mo.) and octylphenol-ethylene oxide condensates (sold under the trade name Nonidet P-40 by Sigma Co., St. Louis, Mo.). Thus, those skilled in the art will recognize that a variety of non-ionic detergents may be used to practice the present invention.

The metal chelating agent added to the permeabilization reagent chelates, or binds, free metal ions such as magnesium, manganese and zinc. While not wishing to be bound by theory, it is believed that chelation of the free metal ions inhibits enzymes, such as nucleases, that may degrade the desired nucleic acid. Metal chelating agents may also dissociate some molecular components of the microbial cell wall. A variety of metal chelating agents are available to serve this purpose. Applicants use EDTA for its low cost and convenience.

Preferably, the permeabilization reagent contains between about 0.01 to about 1% of the non-ionic detergent and between to about 1 mM to about 100 mM EDTA; more preferably 0.07% Triton X-100 and 10 mM EDTA. A 0.07% concentration of Triton X-100 was found to be sufficient to release essentially all of the target ribosomal RNA from *Streptococcus pyogenes*. Moreover, EDTA concentrations greater than 10 mM do not appear to provide any additional benefit.

Although not essential to the practice of the present invention, the permeabilization reagent may contain a weak buffer, preferably the free acid of HEPES (4-(2-Hydroxyethyl)-1-piperazineethane-sulfonic acid), to stabilize the pH of the permeabilization reagent. If the permeabilization reagent is to be prepared and stored for later use, a preservative may also be added to the permeabilization reagent to prevent the growth of undesired microorganisms during the storage period. Preferably, 5.7 mM sodium azide is added. If the desired target nucleic acid is RNA, the pH of the solution should be adjusted to be not greater than 8.0. Preferably, the pH of the permeabilization reagent is adjusted to pH 7.5 by the addition of base, i.e., lithium hydroxide. Buffers which are appropriate for use at a pH below 8.0 other than those disclosed herein are known to those of ordinary skill in the art.

If the cell sample is obtained from a clinical specimen or other source which may cause the sample to contain nucleases, an anionic detergent should also be added to the permeabilization reagent, particularly if the target nucleic acid is RNA. An anionic detergent is a detergent that is negatively charged when dissolved in solution at pH 7.0. Preferably, the permeabilization solution contains 1% (w/v) lithium lauryl sulfate (LLS) in these circumstances. While not wishing to be bound by theory, it is believed that the anionic detergent serves to disrupt or denature any nucleases, especially ribonucleases, found in the clinical specimen or other material thereby preventing the degradation of nucleic acids in the sample. The anionic detergent is not necessary to effect the release of nucleic acids from the cell sample. Lithium lauryl sulphate between about 0.01% and about 2% are preferred; most preferably, the concentration of LLS is between 0.2% and 1%. At lithium lauryl sulfate concentrations greater than 2%, the yield of target nucleic acids is diminished.

Once the cell sample and permeabilization reagent have been mixed, the mixture should be heated in the range 80°–100° C. for 1–30 minutes. Applicants have found that a variety of temperatures above 80° C. are effective. At temperatures below 80° C. the extraction of nucleic acids from the target cells (i.e., *Streptococcus pyogenes*) does not appear to reach completion. Similarly, the period of time the mixture is held at the elevated temperature is relatively short; the extraction of ribosomal RNA from a 300 μl sample containing approximately a million cells of *S. pyogenes*, a Gram-positive bacterium generally considered difficult to lyse, results in a good yield of nucleic acids within 5 minutes at 95° C. Thus, in a preferred embodiment the cell sample/permeabilization reagent mixture is heated for about 5 minutes at about 95° C.

EXAMPLE 1

Comparison of the Present Method with Enzymatic Lysis of *S. pyogenes*

FIG. 1 shows a comparison of the rates of hybridization of *Streptococcus pyogenes* cell preparations which had been subjected to various permeabilization protocols. In this experiment the following methodology was employed; however many variations of the hybridization protocol and detection steps will occur to one of ordinary skill in the art after reading this disclosure, and the specific hybridization and detection methods disclosed herein are for purposes of illustration only.

Eighteen hundred microliters of the permeabilization reagent (7.4 mM HEPES pH 7.5, 0.07% (v/v) Triton X-100, 10 mM disodium EDTA and 5.7 mM sodium azide) was pipetted into a tube. *Streptococcus pyogenes* cells grown on blood agar for 18 hours were washed once in a saline solution, then suspended to $3.0 \times 10^8$ cells per ml. in permeabilization reagent. Two hundred microliters of this cell suspension were diluted into the tube containing the 1800 μl of permeabilization reagent, and the suspension was heated at 95° C.; aliquots of 300 μl were taken from the tube at 5, 10, 15 and 30 minutes and put on ice.

The tubes used for hybridization in this experiment contained a labeled oligonucleotide probe specific to *Streptococcus pyogenes* in a lyophilized probe reagent; these tubes and all subsequent reagents were taken from an AccuProbe Group A Streptococcus culture identification test kit (Gen-Probe, Inc., San Diego, Calif.) unless expressly indicated otherwise. (See AccuProbe package insert, Milliman et al., U.S. Pat. No. 5,232,831; and Arnold et al., U.S. Pat. No. 4,950,613 which are hereby incorporated by reference herein). Because the lyophilized reagent contained lytic enzymes, 50 μl of a solution containing 2% LLS (AccuProbe Reagent 2) was mixed into each tube to denature the lyophilized enzyme; a control tube was given 50 μl of the cell suspension in permeabilization buffer, incubated for 5 minutes at 37° C. to allow enzymatic lysis to occur, then brought up to 100 μl with AccuProbe Reagent 2. Tubes were prepared in quadruplicate for each time point. The rest of the tubes were then given 50 μl of the heat-treated cell suspensions (another control suspension was given the same reagents as the experimental tubes, but was left at room temperature during the heat-treatment step; this was called the "detergent only" control).

Hybridization was promoted by incubating the tubes at 60° C. Two tubes from each time point were incubated for 5 minutes, the remaining pair of tubes for each time point were incubated for 30 minutes. The amount of hybridization, and therefore the amount of detectable target nucleic acids released from the cells was determined by HPA. (See Arnold et al., supra.) Three hundred microliters of Reagent 3 (Selection Reagent) was added to each tube, and the tubes mixed and incubated further at 60° C. for 5 minutes. The chemiluminescence of the hybridized probe was measured in a Leader I luminometer (Gen-Probe, Inc., San Diego, Calif.). The chemiluminescence of the assay samples was expressed in relative light units (RLU) and is directly proportional to the amount of probe that has hybridized to the selected ribonucleic acid.

As can be seen from the graph in FIG. 1, the extraction of the target nucleic acids from the *S. pyogenes* cell samples treated with permeabilization buffer was essentially complete at 5 minutes, since the cell sample mixtures that were heated for 5 minutes had a signal equal to the cell sample mixtures that were heated for 30 minutes. To the Applicants' surprise, the extent of hybridization to target nucleic acids released from the cells incubated with the permeabilization reagent, even for times as short as 5 minutes, was twice that seen with target nucleic acid released from the enzyme-treated cells. This result was completely unexpected and clearly adds to the utility of the present method by demonstrating greater assay sensitivity at a lower cost than with enzymatic lysis steps.

EXAMPLE 2
Estimate of Amount of RNA Liberated

Figure 2:
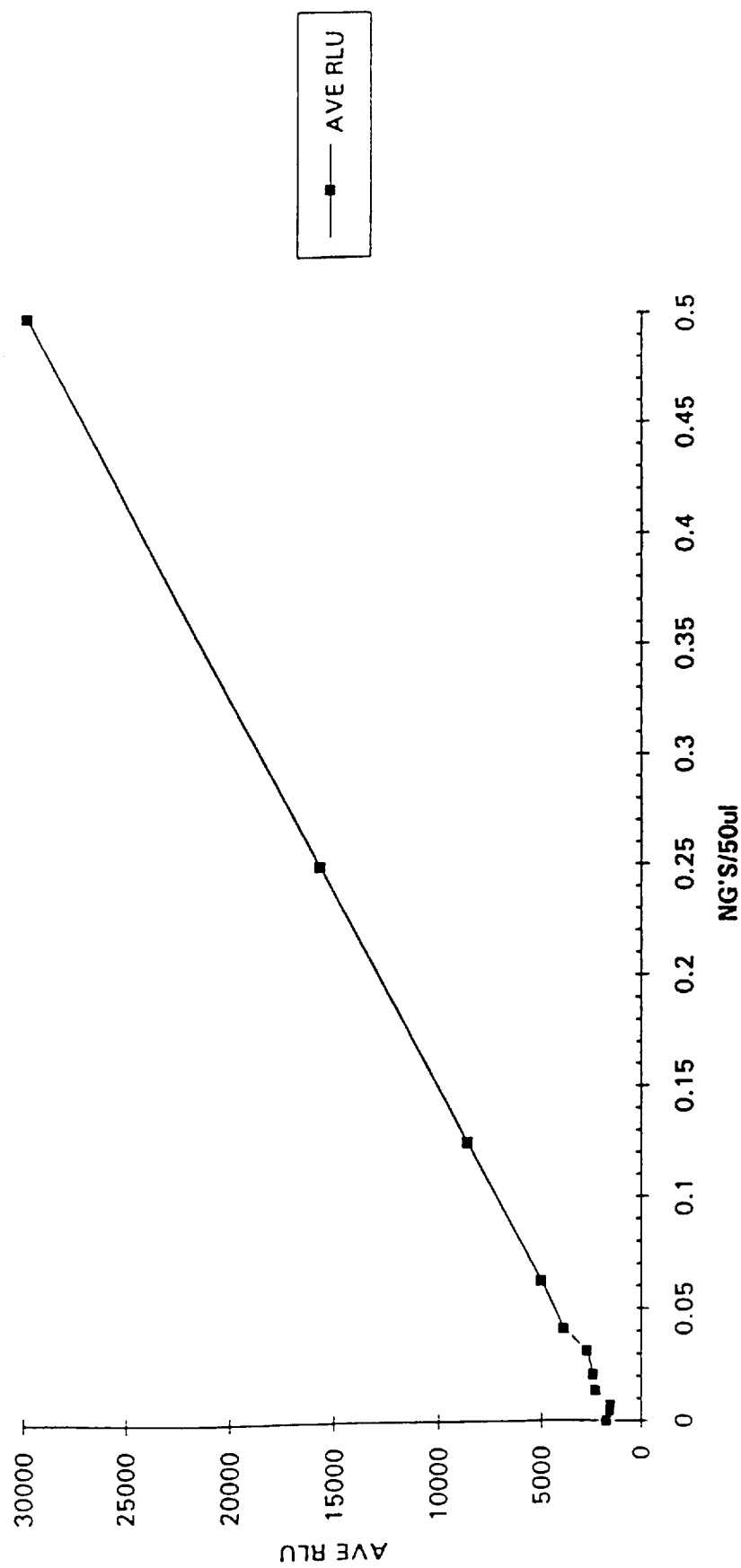
FIG. 2 is a graphical representation of an experiment showing the sensitivity of the hybridization detection system (HPA; described below) to known quantities of added *Streptococcus pyogenes* ribosomal RNA.
Figure 3:
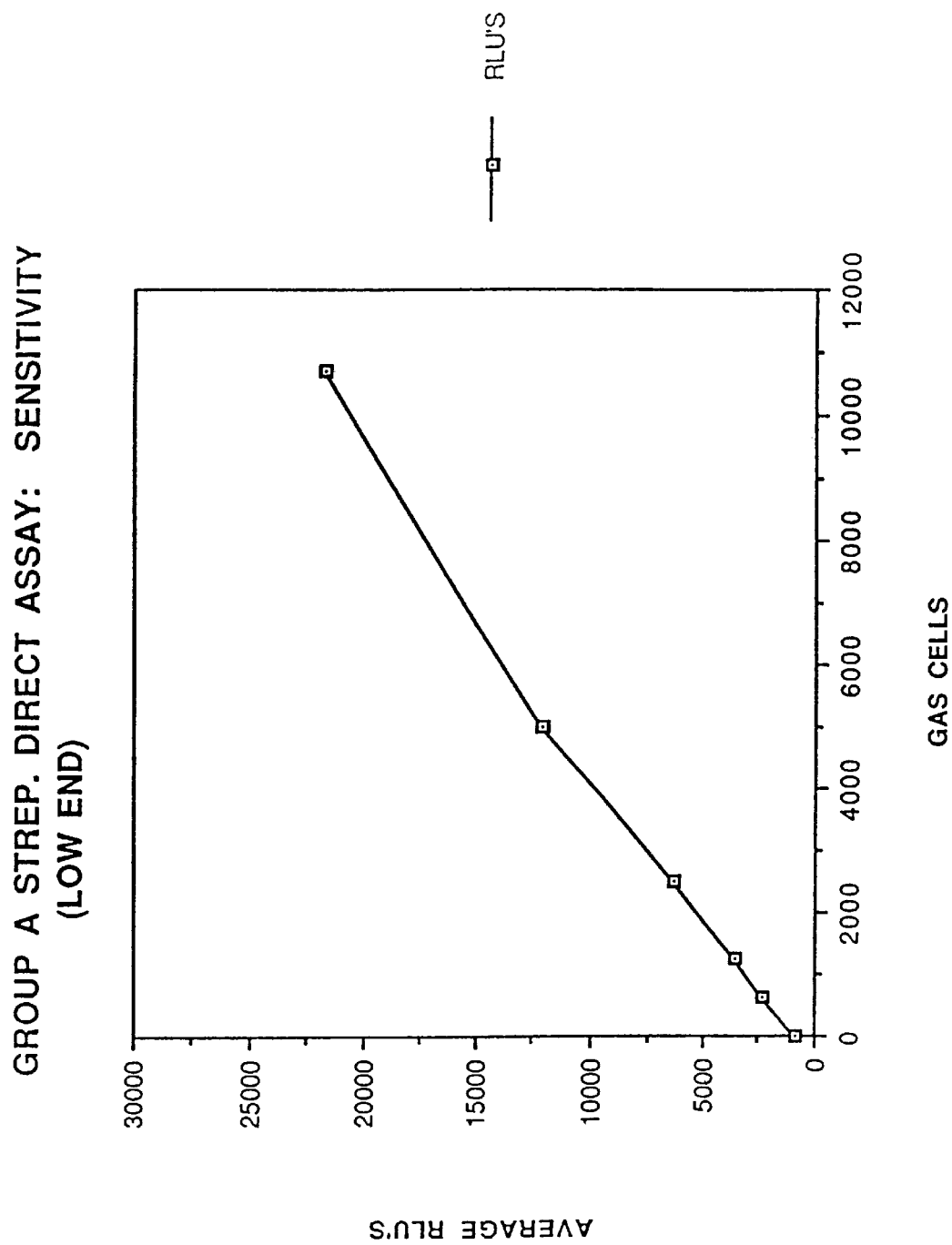
FIG. 3 is a graphical representation demonstrating the results of a hybridization assay performed on dilutions of *Streptococcus pyogenes* cells in which the target ribosomal RNA was released according to the methods described herein.

Applicants believe that by using the preferred method delineated above, nearly all of the cellular ribosomal RNA may be released from the cells during the extraction process. In order to estimate the percentage of total cellular ribosomal RNA released by cells permeabilized by the present methods, Applicants performed the Hybridization Protection Assay (HPA) described below on (a) dilutions of a solution of *S. pyogenes* ribosomal RNA of known concentration and (b) dilutions from a known concentration of *S. pyogenes* cells where nucleic acids were extracted according to the methods of the present invention, and subjected to hybridization as in Example 1. FIG. 2 is a graphical representation demonstrating the results of performing the HPA on dilutions of known amounts of ribosomal RNA. As can be seen, the chemiluminescence of the hybridization products increases proportionally to the amount of ribosomal RNA in the sample. Similarly, FIG. 3 is a graphical representation of the results of performing the HPA on *S. pyogenes* cells in which the nucleic acid was extracted as in FIG. 1. The chemiluminescence of each sample increases proportionally to the number of cells in the sample.

An approximation of the amount of ribosomal RNA liberated from each cell can be calculated by comparing the results from FIGS. 1 and 2. Referring to FIG. 2, 0.25 ng of added *S. pyogenes* ribosomal RNA corresponds to about 15,000 RLU's. Referring to FIG. 3, 15,000 RLU's correspond to about 7300 cells. Dividing 0.25 by 7300 yields the amount of ribosomal RNA detected per cell: 0.000034 ng. This figure is within experimental error of another approximation: that the total amount of ribosomal RNA contained within a bacterial cell is about 0.00002 ng. (See *Handbook of Biochemistry and Biophysics* (CRC Press 1992)). Thus, it is reasonable to conclude that a large percentage, if not all, of the *S. pyogenes* ribosomal RNA is extracted using the permeabilization method of the present invention.

EXAMPLE 3
Effectiveness of the Method to Liberate Both DNA and RNA

In order to demonstrate that the present method will cause cells to release both DNA and RNA, the following experiment was performed. Cultures of *S. pyogenes, Escherichia coli, Candida albicans,* and *Streptococcus agalactiae* were grown for 18 hours on blood agar. Three 10 microliter loopfuls of each organism were suspended in 10 ml of sterile saline solution, then centrifuged for 7 minutes at 2000×g. The supernatant was decanted off, and twelve 1 μl loopfuls of each organism was added to 12 ml of the permeabilization reagent described in Example 1. In addition, a 10-fold dilution of each tube was made in the same reagent. Three hundred microliters of each suspension was given to each of three separate tubes. The first and second tubes of each set was heated for 10 minutes at 95° C. before further treatment. The third tube of each set was left at room temperature for 10 minutes.

The cells were centrifuged for 5 minutes at 10,000×g, and the supernatants were transferred to clean tubes. For each set, the first tube was given 15 μl of sterile saline solution, then incubated for 3 hours at 37° C. The second and third tube of each set were given 25 μl of 4 N NaOH to hydrolyze the RNA, mixed, and incubated for 3 hours at 37° C.

At the end of 3 hours, the second and third tubes were given 70.5 μl of 1 N HCl to bring the pH to 7.0. Tube one was given 70.5 μl of saline solution. All tubes were heated at 95° C. for 5 minutes to denature the double-stranded DNA, then immediately chilled on ice.

The hybridization and assay were done essentially as in Example 1, except a single acridinium ester-labeled probe was used. This probe had a nucleotide sequence that is sufficiently complementary to sequences common to all bacteria and all fungi. Fifty microliters of the probe was added to 50 μl of each sample, and hybridization allowed at 60° C. for 30 minutes. The samples were then treated as in the HPA (hybridization protection assay) procedure, described below and in Arnold, et al, supra.

The results of the experiment are depicted in Table 1 below. The data show that nucleic acids resistant to strong base (i.e. DNA) are liberated from the cells treated in the manner of the present invention. Moreover, a population of the liberated DNA has a specific sequence detectable by nucleic acid hybridization.

TABLE 1

Amounts of RNA and DNA Released According to the Present Invention

| Organism | Tube 1: Released Nucleic acids | Tube 2: Released DNA | Tube 3: Effect of NaOH with no heat-treatment |
| --- | --- | --- | --- |
| S. pyogenes | 135,493,000 | 186,600 | 57,090 |
| S. agalactiae | 113,026,000 | 133,200 | 49,150 |
| C. albicans | 108,126,000 | 198,690 | 82,980 |
| E. coli | 81,212,000 | 595,680 | 119,500 |

EXAMPLE 4
Suitability of the Method to Liberate Nucleic Acids From a Wide Range of Microorganisms In order to determine the effectiveness of the method of the present invention to extract target nucleic acids from a wide range of microorganisms, the permeabilization reagent described in Example 1 was used to treat samples containing identical concentrations of the following microorganisms, which included Gram-positive bacteria, Gram-negative bacteria and yeast. The all bacterial/all yeast probe used in this experiment was non-specific with regard to bacteria and fungi; i.e. the probe had a nucleotide sequence sufficiently complementary to ribosomal RNA sequences common to all bacteria and fungi to hybridize the liberated ribosomal RNA of each microorganism under the hybridization conditions described above. As a negative control, the same organisms were treated according to the method of the present invention, except after the nucleic acid extraction step, a second probe was added to the liberated nucleic acids. The second probe was present in the hybridization mixture at the same concentration as the first probe, and had a nucleotide sequence complementary to a specific nucleotide sequence contained in ribosomal RNA of Group A Streptococcus species only. A positive result (i.e., detection of hybridized probe) was defined as a reading of greater than 1,000,000 RLU in the HPA detection method described above; a negative result was defined as 1,000,000 RLU or less.

FIGS. 4A, 4B and 4C list the panel of microorganisms, all of which were treated according to Example 1, and shows the results of the assay. As can be seen, all the assayed microorganisms, with the exception of S. pyogenes, tested negative in the control experiment. In no case was the negative result for an assayed microorganism greater than 3000 RLU in the HPA detection assay. By contrast, all of the tested microorganisms permeabilized in accordance with the present method released the ribosomal RNA target nucleic acid in sufficient quantities to indicate a clear positive by the all-bacterial/all yeast HPA detection method. The fact that the tested microorganisms included yeast and Gram-positive bacteria as well as various genera of Gram-negative bacteria demonstrates the broad applicability of the present method for samples containing a heterogeneous population of microorganisms, and the effectiveness of using the permeabilization reagent described herein as a generic nucleic acid extraction reagent having applicability in the detection and identification of a wide variety of microorganisms.

EXAMPLE 5
Determining That the Cell Walls are Not Physically Disrupted

Once nucleic acid had been released from the desired cell sample, the cell samples were inspected to determine whether the cell walls have been physically disrupted. There are many methods for examining the integrity of cell walls, including phase-contrast microscopy and the Gram stain, which are described in American Society for Microbiology, *Manual of Methods for General Bacteriology* 8–9 & 26–27 (1981). The indicated portions of this publication are hereby incorporated by reference as part of this disclosure.

The method of the present invention appears very mild to the treated cells. For some uses involving the techniques of molecular biology, e.g. involving nucleic acid amplifications, nucleolytic cleavage, or other enzyme-mediated reactions, it may be desirable that the cell walls of microorganisms not be significantly disrupted. For example, non-nucleic acid cell components may interfere with subsequent manipulation of the extracted nucleic acids. By using the Gram stain one can verify whether the cell walls of a normally Gram-positive microorganism have been physically disrupted.

Preferably, Applicants perform the Gram stain as described in the *Manual of Methods for General Bacteriology*, supra at 27–28. Use of the Gram stain followed by microscopic observation of the stained cells yielded Gram-positive cells which continued to stain purple and maintain their characteristic shape even after permeabilization by the methods of the present invention. This result indicates that the cell wall of the treated bacteria has not been completely physically disrupted. In contrast, enzyme-treated Gram-positive cells stained red or yellow indicating disruption of their cell walls.

EXAMPLE 6
Detecting and Measuring Desired Nucleic Acids

Once the nucleic acids have been released from the specimen, methods are known in the art for detecting and measuring the target nucleic acid(s) using nucleic acid hybridization and detection techniques. For example, nucleic acids may be identified by using a nucleic acid probe sufficiently complementary to a target sequence from the microorganism to be detected, hybridizing the probe to the target nucleic acid sequence, and detecting the double-stranded hybrid of probe and target by methods known to those skilled in the art, such as Southern blots (see Maniatis, T. et al., *Molecular Cloning: A Laboratory Manual,* Cold Springs Harbor Laboratory (1982)) or by the homogeneous solution phase procedure (called the hybridization protection assay or "HPA") described in Arnold et al., Clin. Chem., 35:1588 (1989), and PCT U.S. 88/02746, all of which are hereby incorporated by reference.

The HPA procedure described by Arnold consists of synthesizing an acridinium-ester-labeled DNA probe which can be differentially hydrolyzed based upon selective chemical degradation of the acridinium ester label. The selective chemical degradation is determined by whether the probe is in a hybridized or unhybridized state. The acridinium-ester-label is protected from hydrolysis when the probe is in a hybridized state by interaction with the nucleic acid double-helix. Probe which is not hybridized has its acridinium-ester-label left unprotected from hydrolysis. Thus, chemiluminescence of the acridinium-ester-label associated with unhybridized probe is rapidly lost by the differential hydrolysis, whereas chemiluminescence associated with hybridized probe is minimally affected. The chemiluminescence may be measured by a device, such as a Leader I luminometer (Gen-Probe, Inc., San Diego, Calif.).

Although not essential to practice the present invention, Applicant's preferred method for practicing the HPA method is described.

Reagents The acridinium-ester-labeling reagent is synthesized as follows. Acridine-9-carboxylic acid, obtained from acridine by the method of Lemstedt and Wirth, is added to redistilled thionyl chloride and boiled under reflux for 3 hours, then dried to yield acridine-9-carbonylchloride. Nine mmol of the latter is suspended in 35 ml of anhydrous pyridine. An equimolar amount of benzyl 4-hydroxyphenyl propanoate is added and the mixture stirred over night at room tremperature. The resulting solution is poured into a 1 M solution of HCl. The yellow precipitate is filtered, washed and dried in vacuo. This product, 4-(2-benxyloxycarbonylethyl) phenyl-9-acridine carboxylate (the "benzyl ester"), is recrystalized to yield pale yellow crystals with a melting point of 135° C.

The benzyl ester is dissolved in 10 ml of a $^{45}/_{55}$ (by wieght) hydrogen bromide/acetic acid solution and the resulting mixture is stirred for 2 hours at 50–55° C. The solution is then poured into 100 ml of water. The yellow solid is filtered, washed, and dried as above, then recrystallized in a 50:50 mixture (by volume) of acetonitrile and chloroform to yield 4-(2-carboxyethyl) phenyl-9-acridine carboxylate.

N-hydroxysuccinamide (62 mg) and the yellow solid are dissolved in 5 ml of anhydrous dimethylformamide and cooled to −20° C. N,N'-dicyclohexylcarbodiimide (123 mg) is added, and the mixture incubated at −20° C. for 2 hours, then stirred overnight at room temperature. One drop of glacial acetic acid is added and the dicyclohexylurea is removed by filtration. The solid is recrystalized in benzene/cyclohexane to yield 4-(2-succinimidyloxycarbonylethyl) phenyl-9-acridine carboxylate.

The 4-(2-succinimidyloxycarbonylethyl) phenyl-9-acridine carboxylate is dissolved in 15 ml of anhydrous chloroform and 0.5 ml of methyl fluorosulfonate added and stirred for 18 hours at room temperature. The resulting precipiate is filtered, and washed with anhydrous benzene, which is incorporated herein by reference. Polystyrene or polypropylene tubes (12×75 mm) for assays and chemiluminescence determination are obtained from Sarstedt, Newton, N.C. Chemiluminescence is measured in a Leader I luminometer. All other substances are standard "ultra-pure" or reagent-grade materials.

Methods

Preparation of acridinium-ester-labeled DNA probes. Oligonucleotides are synthesized by use of standard phosphoramidite chemistry. The chemical labeling of the DNA probes with acridinium ester is achieved by reacting alkylamine linker-arms, which were introduced during DNA synthesis, and an N-hydroxysuccinimide ester of a methyl acridinium phenyl ester. Once the acridinium-ester-labeled probes are purified and used in various assay formats, the probe chemiluminescence is detected with a Leader I luminometer as described below.

Hybridization protection assay (HPA). Hybridization reactions are typically carried out at 60° C. in 0.1 M lithium succinate buffer, pH 5.2, containing 1% (w/v) of lithium lauryl sulfate, 2 mM EDTA and 2 mM [ethylenebis (oxyethylenitrilo)]-tetraacetic acid (EGTA) per liter. Hybridization volumes range from 50 to 200 μL and contain from 0.05 to 0.5 pmol of probe. Differential hydrolysis is carried out at 60° C. in sodium tetraborate buffer (0.15–0.20 M), containing 10–50 mL of Triton X-100 surfactant per liter at pH values ranging from 7.0 to 8.5.

In a typical HPA format, the sample containing the target nucleic acid is hybridized with the DNA probe in a 100 μL volume by incubation for 5–10 minutes at 60° C. Applicants then add 300 μL solution of tetraborate buffer and incubate for an additional 5 to 10 minutes at 60° C. After the samples have cooled for a few minutes at room temperature, the chemiluminescence is measured in the luminometer, using one of two automated reagent-injection methods. In method 1, injection of 200 μL of a solution containing 0.1% (v/v) $H_2O_2$ and 1 mM nitric acid is followed, after a 1 second delay, by injection of 200 μL of 1 to 2 M NaOH; the resulting chemiluminescence is integrated for 2 to 5 seconds. In method 2, 200 μL of a 0.1% (V/V) $H_2O_2$ solution containing 1 to 2 M NaOH is injected; the resulting chemiluminescence is integrated for 2 to 5 seconds. All steps in this process, including the hybridization and differential hydrolysis, are carried out in a single 12×75 mm tube.

By the use of a probe detection method such as HPA, the presence or absence of the target nucleic acids can be detected. The acridinium-ester-labeled DNA probe assay is fast, sensitive, easy to use and the backgrounds caused by unhybridized probe are sufficiently low that HPA is useful in the clinical laboratory. Further, the sensitivity of the HPA format makes it of practical use in the clinical laboratory, especially when coupled with the detection of ribosomal RNA, which gives up to a $2×10^4$ enhancement of sensitivity over tests which detect DNA molecules having a single copy of the target sequence.

Kit for Effecting the Present Method

A kit for performing the above method may be prepared from readily available materials and reagents. The kit will include permeabilization reagent, probe reagent, and selection reagent. As will become obvious from reading Applicants' preferred embodiment, this kit can be modified to detect any nucleic acid sequence indicative of a disease, condition or organism, such as a microorganism, etc., simply by selecting the nucleic acid probe in the probe reagent to be a nucleic acid probe specific for the desired application.

Applicants' preferred embodiment is a kit for direct *Streptococcus pyogenes* testing. Preferably, a sample is obtained from a patient's throat by means of a sterile swab. The entire throat swab is be placed into 300 microliters of permeabilization reagent in a polypropylene tube. Applicants' permeabilization reagent is prepared from materials which are all readily available and is composed of 5.7 mM sodium azide, 7.4 mM HEPES(free acid), 0.07% (v/v) Triton X-100, 1% w/v lithium lauryl sulfate, 10 mM EDTA(free acid), and sufficient lithium hydroxide to adjust the permeabilization reagent to a pH of 7.5. When heated to about 95° C. for more than about 30 seconds the permeabilization reagent liberates nucleic acids from *S. pyogenes* cells in the throat swap sample. The specific concentrations and reagents should not be seen as limiting Applicants' invention, as a variety of concentrations and reagents permit successful practice of the present invention. The present disclosure provides guidance for selecting appropriate concentrations, reagents and conditions, and provides specific examples of embodiments of the present invention, which is wholly defined by the claims following this disclosure.

The mixture is then placed on a heating block for 10 minutes at 95° C. After heating, the tube is allowed to cool for 5 minutes at room temperature. The swab is squeezed against the side of the polypropylene tube during the cooling period. After cooling, 50 microliters of the fluid is removed to a clean polypropylene tube. Next, 50 microliters of probe reagent is added to the 50 microliters of sample fluid. Preferably, the probe reagent contains 0.1 M lithium succinate buffer, pH 5.2, 1% (w/v) lithium lauryl sulphate, 2 mM EDTA, 2 mM EGTA and 0.05 pmol of a deoxyribonucleic acid probe specific to a region of the ribosomal RNA of *Streptococcus pyogenes*.

The probe reagent solution is then incubated 30 minutes at 60° C. to allow the acridinium-ester-labeled probe to hybridize to *Streptococcus pyogenes* ribosomal RNA which has been released into solution by the extraction step. After incubation, 300 microliters of selection reagent is added. Preferably, the selection reagent is a 0.15 M sodium tetraborate buffer pH 7.5, containing 0.1% (w/v) Triton X-100.

The resulting solution is thoroughly mixed using a vortex mixer and incubated for 7 minutes at 60° C. so as to allow the differential hydrolysis of the acridinium-ester label. After the final incubation, the probe tube is cooled at least 5 minutes at room temperature before assaying for the presence of hybridized probe. The chemiluminescence is measured in a luminometer and the presence or absence of *Streptococcus pyogenes* in the sample is determined from the reading.

Although nucleic acid extraction and detection methods have been specifically described, it should be understood that other reagents, concentrations and temperatures may be employed without departing from the present invention, and the use of such other reagents, concentrations, and temperatures would be obvious to those skilled in the art after reading the present disclosure. For example, the nucleic acids liberated in accordance with the present method may subsequently be subjected to nucleic acid amplification prior to the selection and detection steps. Therefore, the invention may be embodied, made or used in other specific forms without departing from its spirit or essential characteristics. The present embodiments are thus to be considered in all respects as illustrative and not restrictive. The scope of the invention is indicated by the claims rather than by the foregoing description. All changes which come within the meaning and range of the equivalents of the claims are intended to be embraced therein.

What is claimed is:

1. A method for identifying a wide range of microorganisms in a sample, said method comprising the steps of:
   a) providing to said sample a permeabilization reagent consisting essentially of a non-ionic detergent, an anionic detergent, and a metal chelating agent;
   b) heating said sample at a temperature of from about 80° to about 100° C. so that cells from a wide range of microorganisms present in said sample are permeabilized and release nucleic acids;
   c) providing one or more probe oligonucteotides to said sample under stringent hybridization conditions, each said probe being able to form a detectable hybrid with a target nucleic acid from at least one of said cells under said conditions; and
   d) detecting the presence of one or more of said hybrids as an indication of the identity of one or more microorganisms from said wide range of microorganisms present in said sample,
   wherein said method is conducted in the absence of lysozyme or chaotropes, and shear or mechanical forces are not used to permeabilize said cells.

2. The method of claim 1 wherein said one or more microorganisms belong to the group consisting of Acintobacter species, Actinomyces species, Aerococcus species, Aeromonas species, Alclaigenes species, Bacillus species, Bacteriodes species, Bordetella species, Branhamella species, Bevibacterium species, Campylobacter species, Candida species, Capnocytophagia species, Chromobacterium species, Clostridium species, Corynebacterium species, Cryptococcus species, Deinococcus species, Enterococcus species, Erysielothrix species, Escherichia species, Flavobacterium species, Gemella species, Haemophilus species, Klebsiella species, Lactobacillus species, Lactococcus species, Legionella species, Leuconostoc species, Listeria species, Micrococcus species, Mycobacterium species, Neisseria species, Nocardia species, Oerskovia species, Paracoccus species, Pediococcus species, Peptostreptococcus species, Propionibacterium species, Proteus species, Psuedomonas species, Rahnella species, Rhodococcus species, Rhodospirillium species, Staphlococcus species, Streptomyces species, Streptococcus species, Vibrio species, and Yersinia species.

3. A method for releasing nucleic acids from cells belonging to at least one microorganism from the group consisting of Gram-positive bacteria, Gram-negative bacteria and yeast, said method comprising the steps of:
   a) contacting said microorganism with a permeabilization reagent consisting essentially an anionic detergent at a concentration of between about 0% and about 2% of said permeabilization reagent, a non-ionic detergent, and a metal chelating agent; and
   b) heating said microorganism and said permeabilization reagent together at a temperature of from about 80° to about 100° C. so that cells from said microorganism are permeabilized and release nucleic acids,
   wherein said permeabilization reagent can be the same whether said microorganism is a Gram-positive bacterium, a Gram-negative bacterium or a yeast, and
   wherein said method is conducted in the absence of lysozyme or chaotropes and shear or mechanical forces are not used to permeabilize said cells.

4. The method of claim 3, wherein said microorganism belongs to the group consisting Acintobacter species, Actinomyces species, Aerococcus species, Aeromonas species, Alclaigenes species, Bacillus species, Bacteriodes species, Bordetella species, Branhamella species, Bevibacterium species, Campylobacter species, Candida species, Capnocytophagia species, Chromobacterium species, Clostridium species, Corynebacterium species, Cryptococcus species, Deinococcus species, Enterococcus species, Erysielothrix species, Escherichia species, Flavobacterium species, Gemella species, Haemophilus species, Klebsiella species, Lactobacillus species, Lactococcus species, Legionella species, Leuconostoc species, Listeria species, Micrococcus species, Mycobacterium species, Neisseria species, Nocardia species, Oerskovia species, Paracoccus species, Pediococcus species, Peptostreptococcus species, Propionibacterium species, Proteus species, Psuedomonas species, Rahnella species, Rhodococcus species, Rhodospirillium species, Staphlococcus species, Streptomyces species, Streptococcus species, Vibrio species, and Yersinia species.

5. A method for diagnosing a disease or condition in a human or animal host, said method comprising the steps of:
   a) obtaining a clinical sample from said host;
   b) providing to said sample a permeabilization reagent consisting essentially of an anionic detergent at a concentration of between about 0% and about 2% of said permeabilization reagent, a non-ionic detergent, and a metal chelating agent;
   c) heating said sample at a temperature of from about 80° to about 100° C. so that cells causing or contributing to said disease or condition are permeabilized and release nucleic acids; and
   d) detecting the presence or absence of target nucleic acids from said cells as an indication of the presence or absence of said disease or condition in said host,
   wherein said method is conducted in the absence of lysozyme or chaotropes and shear or mechanical forces are not used to permeabilize said cells.

6. The method of claim 5, wherein said cells are belong to the group consisting of Acintobacter species, Actinomyces species, Aerococcus species, Aeromonas species, Alclaigenes species, Bacillus species, Bacteriodes species, Bordetella species, Branhamella species, Bevibacterium species, Campylobacter species, Candida species, Capnocytophagia species, Chromobacterium species, Clostridium species, Corynebacterium species, Cryptococcus species, Deinococcus species, Enterococcus species, Erysielothrix species, Escherichia species, Flavobacterium species, Gemella species, Haemophilus species, Klebsiella species, Lactobacillus species, Lactococcus species, Legionella species, Leuconostoc species, Listeria species, Micrococcus species, Mycobacterium species, Neisseria species, Nocardia species, Oerskovia species, Paracoccus species, Pediococcus species, Peptostreptococcus species, Propionibacterium species, Proteus species, Psuedomonas species, Rahnella species, Rhodococcus species, Rhodospirillium species, Staphlococcus species, Streptomyces species, Streptococcus species, Vibrio species, and Yersinia species.

7. A method for detecting the presence of an organism in a human or animal host, said method comprising the steps of:
   a) obtaining a clinical sample from said host;
   b) providing to said sample a permeabilization reagent consisting essentially of an anionic detergent at a concentration of between about 0% and about 2% of said permeabilization reagent, a non-ionic detergent, and a metal chelating agent;
   c) heating said sample at a temperature of from about 80° to about 100° C. so that cells from said organism are permeabilized and release nucleic acids; and d) detecting the presence or absence of target nucleic acids from said cells as an indication of the presence or absence of said organism in said host, wherein said method is conducted in the absence of lysozyme or chaotropes and shear or mechanical forces are not used to permeabilize said cells.

8. The method of claim 7 wherein said organism belongs to the group consisting of Acintobacter species, Actinomyces species, Aerococcus species, Aeromonas species, Alclaigenes species, Bacillus species, Bacteriodes species, Bordetella species, Branhamella species, Bevibacterium species, Campylobacter species, Candida species, Capnocytophagia species, Chromobacterium species, Clostridium species, Corynebacterium species, Cryptococcus species, Deinococcus species, Enterococcus species, Erysielothrix species, Escherichia species, Flavobacterium species, Gemella species, Haemophilus species, Klebsiella species, Lactobacillus species, Lactococcus species, Legionella species, Leuconostoc species, Listeria species, Micrococcus species, Mycobacterium species, Neisseria species, Nocardia species, Oerskovia species, Paracoccus species, Pediococcus species, Peptostreptococcus species, Propionibacterium species, Proteus species, Psuedomonas species, Rahnella species, Rhodococcus species, Rhodospirillium species, Staphlococcus species, Streptomyces species, Streptococcus species, Vibrio species, and Yersinia species.

9. A method for identifying a wide range of microorganisms in a sample suspected of containing at least one of said microorganisms, said method comprising the steps of:

a) providing to said sample a permeabilization reagent consisting essentially of an anionic detergent at a concentration of between about 0% and about 2% of said permeabilization reagent, a non-ionic detergent, and a metal chelating agent;

b) heating said sample at a temperature of from about 80° to about 100° C. so that cells from said at least one microorganism are permeabilized and release nucleic acids;

c) providing to said sample one or more probe oligonucleotides under stringent hybridization conditions, each said probe being able to form a detectable hybrid with a target nucleic acid from said cells under said conditions; and d) detecting the presence of one or more of said hybrids as an indication of the identity of said at least one microorganism present in said sample, wherein said method is conducted in the absence of lysozyme or chaotropes and shear or mechanical forces are not used to permeabilize said cells.

10. The method of claim 9, wherein said at least one microorganism is selected from the group consisting of selected from the group consisting of Acintobacter species, Actinomyces species, Aerococcus species, Aeromonas species, Alclaigenes species, Bacillus species, Bacteriodes species, Bordetella species, Branhamella species, Bevibacterium species, Campylobacter species, Candida species, Capnocytophagia species, Chromobacterium species, Clostridium species, Corynebacterium species, Cryptococcus species, Deinococcus species, Enterococcus species, Erysielothrix species, Escherichia species, Flavobacterium species, Gemella species, Haemophilus species, Klebsiella species, Lactobacillus species, Lactococcus species, Legionella species, Leuconostoc species, Listeria species, Micrococcus species, Mycobacterium species, Neisseria species, Nocardia species, Oerskovia species, Paracoccus species, Pediococcus species, Peptostreptococcus species, Propionibacterium species, Proteus species, Psuedomonas species, Rahnella species, Rhodococcus species, Rhodospirillium species, Staphlococcus species, Streptomyces species, Streptococcus species, Vibrio species, and Yersinia species.

11. The method of any one of claims 1, 3, 5, 7 and 9, wherein the cell wall of a majority of said cells is not disrupted.

12. The method of any one of claims 1, 3, 5, 7 and 9, wherein said heating step is performed for about 1 to 30 minutes.

13. The method of any one of claims 1, 3, 5, 7 and 9, wherein the concentration of said anionic detergent is between about 0.2% and about 1% of said permeabilization reagent.

14. The method of any one of claims 1, 5, 7 and 9, wherein said target nucleic acid(s) comprises ribosomal RNA.

15. The method of any one of claims 1, 3, 5, 7 and 9, wherein said non-ionic detergent is selected from the group consisting of polyoxyethylene alcohols and octylphenol-ethylene oxide condensates.

16. The method of claim 15, wherein said non-ionic detergent is a polyoxyethylene alcohol.

17. The method of claim 15, wherein said non-ionic detergent is an octylphenol-ethylene oxide condensate.

18. The method of claim 15, wherein the concentration of said non-ionic detergent is between about 0.01% and about 1%.

19. The method of any one of claims 1, 3, 5, 7 and 9, wherein said ionic detergent is a water-soluble lauryl sulfate salt.

20. The method of claim 19, wherein said ionic detergent is selected from the group consisting of sodium dodecyl sulfate and lithium lauryl sulphate.

* * * * *